United States Patent [19]
Merkle et al.

[11] Patent Number: 4,868,308
[45] Date of Patent: Sep. 19, 1989

[54] PREPARATION OF N-PHENYL(PYRIDYL) SULFONYLDIAMIDES

[75] Inventors: Hans Merkle; Albrecht Mueller, both of Ludwigshafen; Gerhard Hamprecht, Weinheim; Gernot Reissenweber, Boehl-Iggelheim, all of Fed. Rep. of Germany

[73] Assignee: BASF Aktiengesellschaft, Ludwigshafen, Fed. Rep. of Germany

[21] Appl. No.: 119,255

[22] Filed: Nov. 6, 1987

Related U.S. Application Data

[63] Continuation of Ser. No. 748,459, Jun. 25, 1985, abandoned.

[30] Foreign Application Priority Data

Jun. 30, 1984 [DE] Fed. Rep. of Germany ....... 3424186
Aug. 4, 1984 [DE] Fed. Rep. of Germany ....... 3428837

[51] Int. Cl.$^4$ .................... C07D 213/02; C07C 143/78
[52] U.S. Cl. ...................................... 546/310; 560/13; 562/430; 564/79
[58] Field of Search .......................... 546/310; 560/13; 562/430; 564/79

[56] References Cited

U.S. PATENT DOCUMENTS 3,822,257  7/1974  Hamprecht et al. ............ 260/243 R
3,935,201  1/1976  Mangold et al. ................ 260/243 R
4,438,276  3/1984  Stabile et al. ........................ 560/13

FOREIGN PATENT DOCUMENTS 0070467  1/1983  European Pat. Off. .

OTHER PUBLICATIONS

March, J., Advanced Organic Chemistry, 3rd Edition, 1985.

Primary Examiner—Mary C. Lee
Assistant Examiner—Zinna Northington
Attorney, Agent, or Firm—Keil & Weinkauf

[57] ABSTRACT

A process for the preparation of N-phenyl(pyridyl)sulfonyldiamides by reacting a 2-aminobenzoic acid (nicotinic acid) derivative with sulfur trioxide, chlorosulfonic acid or an adduct of sulfur trioxide with a tertiary amine in the presence of a diluent and of a tertiary amine, and reacting the resulting sulfamate with a primary amine and a phosphorus halide, or by reacting a 2-aminobenzoic acid (nicotinic acid) derivatives with an N-alkyl(cycloalkyl)sulfamic acid or a salt of this acid in the presence of a diluent and of a phosphorus halide.

7 Claims, No Drawings

PREPARATION OF N-PHENYL(PYRIDYL) SULFONYLDIAMIDES

This application is a continuation of application Ser. No. 748,459, filed on June 25, 1985, now abandoned.

The present invention relates to a process for the preparation of N-phenyl(pyridyl)sulfonyldiamides by reacting a 2-aminobenzoic acid (nicotinic acid) derivative with sulfur trioxide, chlorosulfonic acid or an adduct of sulfur trioxide with a tertiary amine in the presence of a diluent and of a tertiary amine, and reacting the resulting sulfamate with a primary amine and a phosphorous halide, or by reacting a 2-aminobenzoic acid (nicotinic acid) derivative with an N-alkyl(cycloalkyl)sulfamic acid or a salt of this acid in the presence of a diluent and of a phosphorus halide.

It has been disclosed that N-(2-methoxycarbonylphenyl)-N'-isopropylsulfonyldiamide can be prepared by reacting methyl anthranilate with chlorosulfonic acid in the presence of a pyridine base, which also serves as a diluent, and reacting the resulting sulfamate with isopropylamine in the presence of phosphorus pentoxide as a dehydrating agent (European Laid-Open Application No. 0,070,467). This process has a number of disadvantages which make it difficult to carry out particularly on an industrial scale. Because of unfavorable proportions of the reactants (a large excess), working up of the reaction mixture requires expensive apparatus and entails large losses. Moreover, the use of phosphorus pentoxide results in a heterogeneous reaction mixture; hydrolysis of the phosphorus pentoxide by the water liberated gives a lumpy precipitate which blocks the apparatus and makes an optimum reaction procedure impossible.

We have found that N-phenyl(pyridyl)sulfonyldiamides of the formula

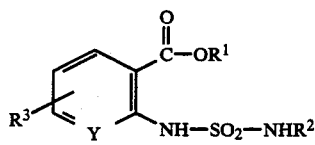

(I)

where $R^1$ is hydrogen or $C_1$–$C_5$-alkyl, $R^2$ is $C_1$–$C_5$-alkyl or $C_3$–$C_8$-cycloalkyl, $R^3$ is hydrogen, $C_1$–$C_{10}$-alkyl or $C_1$–$C_4$-haloalkyl and Y is CH or N, can advantageously be obtained starting from a 2-aminobenzoic acid (nicotinic acid) derivative if a 2-aminobenzoic acid (nicotinic acid) derivative of the formula

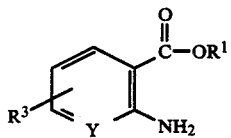

(II)

where $R^1$, $R^3$ and Y have the above meanings, (a) is reacted with sulfur trioxide, chlorosulfonic acid or an adduct of sulfur trioxide with a tertiary amine in the presence of a tertiary amine A and of a diluent to give the corresponding sulfamate, and the latter is reacted with a primary amine of the formula

$R^2$—$NH_2$ (III)

where $R^2$ has the above meanings, in the presence of a phosphorus halide as a dehydrating agent, or (b) is reacted with a sulfamic acid of the formula

$R^2$—NH—$SO_3H$ (IV)

where $R^2$ has the above meanings, or with a salt of this acid, in the presence of a tertiary amine A, a diluent and a phosphorus halide as a dehydrating agent.

Compared with the prior art processes, in which phosphorus pentoxide is used as the dehydrating agent, the processes according to the invention give the N-phenyl- and N-pyridylsulfonyldiamides in high purity and yield. A lower yield, as well as side reactions due to phosphoramide formation and secondary reactions initiated by this, would have been expected, particularly when using phosphorus oxychloride as a dehydrating agent (Houben-Weyl, Methoden der organ. Chemie, Vol. 12/2, page 386, 4th Edition, 1964).

Process (a) can be represented by the following equation:

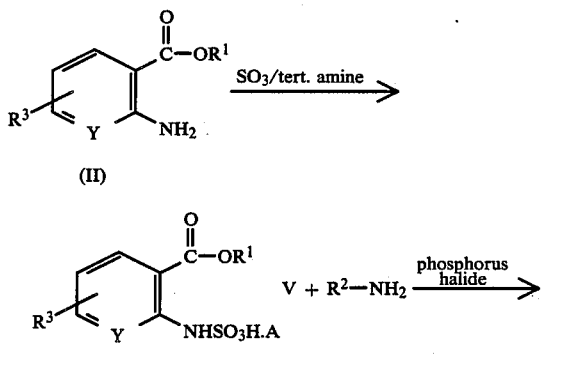

Process (b) can be represented by the following equation:

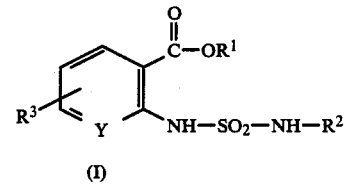

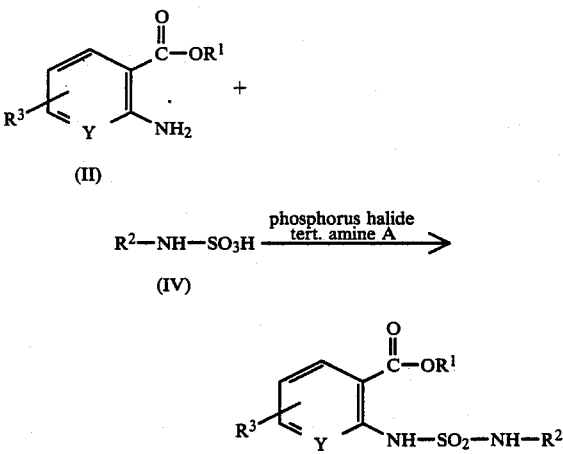

Suitable tertiary amines A are trialkylamines, preferably those containing $C_1$–$C_4$-alkyl groups, eg. trimethylamine, triethylamine, dimethylethylamine, dimethyl-n-propylamine, tri-n-propylamine, triisopropylamine, tri-n-butylamine, triisobutylamine or dimethyl-n-butylamine, N,N-dialkyl-N-cycloalkylamines, preferably those containing $C_1$–$C_4$-alkyl groups and $C_6$–$C_8$-cycloalkyl groups, eg. N,N-dimethyl-N-cyclohexylamine, N,N-dialkylanilines, preferably those containing $C_1$–$C_4$-alkyl groups, in particular methyl or ethyl, eg. N,N-dimethylaniline, N,N-diethylaniline or N-methyl-N-ethylaniline, heterocyclic tertiary amines, such as N-alkylmorpholines, N-alkylpiperidines, N-alkylimidazoles, N-alkylpyrroles, alkylpyridines and dialkylpyridines, each preferably containing $C_1$–CHD 4-alkyl substituents, in particular methyl or ethyl, eg. N-methylmorpholine, N-ethylmorpholine, N-methylpiperidine, N-ethylimidazole, N-methylpyrrole, α-, β- and γ-picoline, 2,4-lutidine and 2,6-lutidine, as well as quinoline, quinaldine and pyridine. Mixtures of these tertiary amines may also be used. Preferred amines are trialkylamines and N,N-dialkyl-N-cycloalkylamines.

Phosphorus halides which are suitable as dehydrating agents are phosphorus pentachloride, phosphorus trichloride and phosphorus oxychloride, in particular the last-mentioned compound.

Suitable diluents are both polar and non-polar compounds, for example halohydrocarbons, such as methylene chloride, 1,1- and 1,2-dichloroethane, 1,2-cis-dichloroethylene, 1,1-, 1,2- and 1,3-dichloropropane, 1,4-dichlorobutane, carbon tetrachloride, tetrachloroethane, 1,1,1-a dn 1,1,2-trichloroethane, trichloroethylene, pentachloroethane, trichlorofluoromethane, chlorobenzene, dichlorobenzenes, such as o-, m- and p-dichlorobenzene, chlorotoluenes, such as o-, m- and p-chlorotoluene, dichlorotoluenes, such as 2,4-dichlorotoluene, trichlorobenzenes, such as 1,2,4-trichlorobenzene, ethers, such as ethylene glycol dimethyl ether, diethyl ether, di-n-propyl ether or methyl tert.-butyl ether, nitrohydrocarbons, such as nitromethane, nitrobenzene, o-, m- and p-chloronitrobenzenes or o- or p-nitrotoluenes, hydrocarbons, such as benzene, toluene, xylene, hexane, heptane, or octane, tetraalkylureas, such as tetramethylurea, and N,N-dialkylamides, such as dimethylformamide, or mixtures of such diluents. Advantageously, halohydrocarbons or ethers, in particular dichloroethane, chlorobenzene or ethylene glycol dimethyl ether, are used. The amount of diluent advantageously varies from 1,500 to 3,000 parts by weight per mole of starting material of formula II.

It is also possible to employ an excess of tertiary amine A as the diluent, instead of using an additional diluent. Preferred amines for this purpose are tertiary amines, such as α-picoline, β-picoline, γ-picoline, 2,4-lutidine or 2,6-lutidine.

In addition to sulfur trioxide and chlorosulfonic acid, adducts of sulfur trioxide with tertiary amines are also suitable for the preparation of the sulfamic acid intermediate in process (a). Suitable adducts here are adducts of sulfur trioxide with one of the abovementioned tertiary amines A, preferably adducts of sulfur trioxide with α-picoline, pyridine, triethylamine, N,N-dimethyl-N-cyclohexylamine, for example a triethylamine/$SO_3$ or N,N-dimethyl-N-cyclohexylamine/$SO_3$ adduct. These adducts can be prepared by adding sulfur trioxide or chlorosulfonic acid to a solution of the tertiary amine in one of the above diluents at from $-20°$ to $+50°$ C., preferably from $-10°$ to $+30°$ C. It is also possible initially to take a solution of the sulfur trioxide or of the chlorosulfonic acid and to add the tertiary amine in the stated temperature range.

The reaction according to process (a) is advantageously carried out by reacting from 1 to 2.2, preferably from 1.3 to 2, moles of sulfur trioxide or chlorosulfonic acid with from 2 to 6, preferably from 2.5 to 5, moles of the tertiary amine at from $-20°$ to $+100°$ C., preferably from $-10°$ to $+60°$ C., in the presence of the diluent. One mole of the 2-aminobenzoic acid (nicotinic acid) derivative of the formula II, as such or dissolved or suspended in a diluent suitable for the reaction, is then added to the resulting solution or suspension of the sulfur trioxide/amine adduct (or chlorosulfonic acid/amine adduct) at from $-20°$ to $+100°$ C., preferably from $+10°$ to $+60°$ C. After a few minutes, the salt of the corresponding sulfamic acid with the base is formed, this salt being present as a suspension or solution, depending on the reaction conditions. The sulfamic acid may also be prepared by adding the $SO_3$ adduct as such to a suspension or solution of the 2-aminobenzoic acid (nicotinic acid) derivative in one of the above diluents.

The condensation of the sulfamate with the primary amine of the formula III under the water-eliminating action of a phosphorus halide is advantageously carried out at from 0° to $+100°$ C., preferably from $+10°$ to $+80°$ C. The amount of primary amine is from 1 to 4, preferably from 1.2 to 3.8, moles per mole of the acid derivative of the formula II. The amine is run slowly into the reaction mixture, which is at from $+10°$ to $+100°$ C., preferably from $+20°$ to $+70°$ C., after which from 0.7 to 3, preferably from 1 to 3, in particular from 1.3 to 2.5, moles of a phosphorus halide are added at from 0° to $+100°$ C., preferably from $+10°$ to 80° C. After the reaction has proceeded for a short time at from room temperature to the boiling point, the reaction mixture is hydrolyzed with water and worked up. All reactions can be carried out batchwise or continuously, under atmospheric or superatmospheric pressure.

In process (b), the starting materials can be reacted with one another in stoichiometric amounts or in excess, preferably in a ratio of from 1.1 to 3, in particular from 1.1 to 2, moles of sulfamate of the formula IV per mole of the acid derivative of the formula II. Instead of the sulfamic acid of formula IV, or its salts, which are preferably salts of the formula $R^2$—NH—$SO_3H$—A, where A is one of the abovementioned tertiary amines, it is also possible to use reaction mixtures of primary amines of the formula III, sulfur trioxide or chlorosulfonic acid and a tertiary amine A. These mixtures contain from 0.5 to 2.5, preferably from 0.6 to 1.5, moles of sulfur trioxide or chlorosulfonic acid and from 1 to 5, preferably from 1.5 to 4, moles of the tertiary amine A per mole of the amine of the formula III. The formation of the sulfamate of the formula IV is carried out, as a rule, at from $-20°$ to $+100°$ C., preferably from $-10°$ to $+60°$ C., batchwise or continuously, under atmospheric or superatmospheric pressure. Advantageously, the amine of the formula III is run into a solution or suspension of the sulfonating agent in one of the above diluents, but the addition may also be effected in the reverse order.

It is not necessary to isolate the resulting sulfamic acid or its salts; instead, the reaction mixture is advantageously reacted directly with the 2-aminobenzoic acid (nicotinic acid) derivative of the formula II, so that the sulfamic acid, or its salt, is only formed in situ.

The condensation of the acid derivative of the formula II with the sulfamate of the formula IV is carried out, as a rule, at from +10° to +100° C., preferably from +20° to +80° C., continuously or batchwise. In this procedure, the ester is run into a solution or suspension of the sulfamate at from +20° to +45° C., the mixture is heated to from +45° to +60° C., the phosphorus halide is added, and the mixture is heated to from +60° to +80° C. and stirred for a further 1-2 hours.

When the reaction is complete, and where a water-miscible diluent has been used, the N-phenyl(pyridyl)sulfonyldiamide of the formula I can very readily be isolated from the reaction mixture by evaporating the latter to dryness and then treating the residue with water or diluent hydrochloride acid. If a water-immiscible diluent has been used, the mixture can be extracted with, for example, dilute hydrochloric acid or water, and the solution can be chromatographed if necessary and then evaporated to dryness. However, it is also possible first to carry out evaporation and then to wash the residue in succession with dilute hydrochloric acid and with water.

The 2-aminobenzoic acid (nicotinic acid) derivatives of the formula II which are required as starting materials, and the primary amines of the formula III, are known from the literature or can be synthesized by conventional methods (Beilstein, Vol. 14, page 318, and Vol. 22, page 542).

The sulfamic acids of the formula IV and their salts can be prepared not only by reacting a primary amine of the formula III with sulfur trioxide or chlorosulfonic acid in the presence of a tertiary amine but also by reacting an alkyl isocyanate with sulfuric acid (Angew. Chem. 93 (1981), 151-163).

The N-phenyl(pyridyl)sulfonyldiamides which can be prepared by the novel process are useful intermediates in the synthesis of active ingredients for crop protection and of pharmaceutical compounds. For example, N-(2-alkoxycarbonylphenyl)-N'-isopropylsulfonyldiamides are intermediates for the herbicidal active ingredient B 3-isopropyl-1H-2,1,3-benzothidiazin-(4)-3-one 2,2-dioxide, which can be obtained from these diamides by cyclization with a sodium alcoholate (German Laid-Open Application DOS No. 2,357,063). N-(3-Alkoxycabonylpyrid-2-yl)-N'-isopropylsulfonyldiamides react with the sodium alcoholate to give 3-isopropyl-1H-pyridino[3,2-e]-2,1,3-thiadiazin-4(3H)-one 2,2-dioxides (German Laid-Open Application DOS No. 2,430,353).

In the sulfonyldiamides of the formula I which are prepared according to the invention, $R^1$ is hydrogen or straight-chain or branched $C_1$-$C_5$-alkyl, preferably $C_1$-$C_5$-alkyl, such as methyl, ethyl, n-propyl, isopropyl, n-butyl, sec.-butyl, n-pentyl or isopentyl, $R^2$ is straight-chain or branched $C_1$-$C_5$-alkyl or is $C_3$-$C_8$-cycloalkyl, such as methyl, ethyl, isopropyl, n-butyl, n-pentyl, cyclohexyl or cyclooctyl, $R^3$ is hydrogen, straight-chain or branched $C_1$-$C_{10}$-alkyl, preferably $C_1$-$C_4$-alkyl, or straight-chain or branched $C_1$-$C_4$-haloalkyl, preferably halomethyl, such as methyl, ethyl, isopropyl, n-butyl, n-hexyl, n-decyl or trifluoromethyl, and Y is CH or N. In the case of the N-phenylsulfonyldiamides, $R^3$ is alkyl, or haloalkyl ortho or meta to the amine function on the phenyl ring. In the case of the N-pyridylsulfonyldiamides, $R^3$ is preferably hydrogen.

The meanings of the substituents $R^1$, $R^2$, $R^3$ and Y stated by way of example also apply to the formulae II, III and IV for the starting materials.

The Examples which follow illustrate the process according to the invention. Parts are by weight.

EXAMPLE 1

220 parts of chlorobenzene, 63.5 parts of N,N-dimethyl-N-cyclohexylamine and 19.3 parts of isopropylamine are initially taken and 23.3 parts of chlorosulfonic acid are added dropwise to the solution at from −10° to 0° C. in the course of 30 minutes. Stirring is continued for 30 minutes, a temperature of about 10° C. being established, after which 15.1 parts of methyl anthranilate are added dropwise in the course of 15 minutes and stirring is then continued for 30 minutes at from 50° to 55° C.

The mixture is then cooled to room temperature, 30.6 parts of phosphorus oxychloride are added, and stirring is continued for 30 minutes at from 85° to 90° C. The reaction mixture is cooled to 50° C. and stirred thoroughly at this temperature with 300 parts of water for 15 minutes. The phases are separated, the organic phase is evaporated down in a rotary evaporator, the residue is treated with 1,500 parts of water, and the product is filtered off and dried. 27 parts (98.7% of theory) of 99.5% pure (HPLC) N-(2-methoxycarbonylphenyl)-N'-isopropylsulfonyldiamide of melting point 106° C. are obtained.

EXAMPLE 2

17.5 parts of chlorosulfonic acid are added dropwise to a solution of 173 parts of ethylene glycol dimethyl ether and 141 parts of α-picoline in the course of 30 minutes at from −10° to 0° C. The mixture is stirred for 30 minutes, a temperature of about 10° C. being established, after which 15.1 parts of methyl anthranilate are added dropwise in the course of 15 minutes, during which the temperature is allowed to increase to 25° C. Thereafter, 19.3 parts of isopropylamine are added dropwise in the course of 30 minutes, the temperature being allowed to increase to 30°-35° C., and stirring is then continued for 30 minutes at from 50° to 55° C.

The reaction mixture is cooled to room temperature and 23 parts of phosphorus oxychloride are added. Stirring is continued for a further 30 minutes at from 85° to 90° C., after which the mixture is cooled to about 30° C. and the ethylene glycol dimethyl ether is distilled off in a rotary evaporator. The residue obtained is treated in 800 parts of 10% strength hydrochloric acid and then with 1,000 parts of water, and the product is filtered off and dried. 26.3 parts (91.9% of theory) of 95.1% pure N-(2-methoxycarbonylphenyl)-N'-isopropylsulfonyldiamide of melting point 104° C. are obtained.

EXAMPLE 3

17.5 parts of chlorosulfonic acid are added dropwise to a solution of 173 parts of ethylene glycol dimethyl ether, 93.1 parts of α-picoline and 17.7 parts of isopropylamine in the course of 30 minutes at from −10° to 0° C. Stirring is carried out for 30 minutes, a temperature of about 10° C. being established, after which 15.1 parts of methyl anthranilate are added dropwise in the course of 15 minutes. Stirring is then continued for 30 minutes at from 50° to 55° C. 23 parts of phosphorus oxychloride are then added at room temperature, and stirring is continued for a further 30 minutes at from 85° to 90° C.

The mixture is cooled to about 30° C., after which the ethylene glycol dimethyl ether is distilled off in a rotary evaporator, the resulting residue is treated with 800 parts of 10% strength HCl and then with 1,000 parts of water, and the product is filtered off and dried. 27.8 parts (93.3% of theory) of 91.3% pure N-(2-methoxycarbonylphenyl)-N'-isopropylsulfonyldiamide of the melting point 101° C. are obtained.

EXAMPLE 4

23.3 parts of chlorosulfonic acid are added dropwise to a solution of 220 parts of chlorobenzene, 50.5 parts of triethylamine and 19.3 parts of isopropylamine in the course of 30 minutes at from −10° to 0° C. The mixture is stirred for 30 minutes, a temperature of about 10° C. being established, after which 15.1 parts of methyl anthranilate are added dropwise in the course of 15 minutes and stirring is then continued for 30 minutes at from 50° to 55° C.

23 parts of phosphorus oxychloride are then added at room temperature, and the reaction mixture is stirred for a further 30 minutes at from 85° to 90° C. and then cooled to about 50° C., 300 parts of water are added and the mixture is then stirred thoroughly for 15 minutes. The phases are separated, and the organic phase is then evaporated down in a rotary evaporator.

Thorough stirring in 1,000 parts of water at 50° C. gives 26.8 parts (95.1% of theory) of 96.6% pure N-(2-methoxycarbonylphenyl)-N'-isopropylsulfonyldiamide of melting point 103° C.

EXAMPLE 5

12 parts of sulfur trioxide are added dropwise to a solution of 250 parts of 1,2-dichloroethane, 93.1 parts of α-picoline and 17.7 parts of isopropylamine in the course of 30 minutes at from −10° to 0° C. The mixture is stirred for 30 minutes, a temperature of about 10° C. being established, after which 15.1 parts of methyl anthranilate are added dropwise in the course of 15 minutes, and stirring is then continued for a further 30 minutes at from 50° to 55° C. 23 parts of phosphorus oxychloride are then added at room temperature, and the reaction mixture is stirred for a further 30 minutes at from 85° to 90° C. and then cooled to about 50° C., 300 parts of water are added and the mixture is then stirred thoroughly for 15 minutes. The phases are separated, and the organic phase is then evaporated down in a rotary evaporator. The residue is treated with 1,200 parts of water, and the product is filtered off and dried. 25.4 parts (89.6% of theory) of 96% pure N-(2-methoxycarbonylphenyl)-N'-isopropylsulfonyldiamide of melting point 103° C. are obtained.

EXAMPLE 6

17.5 parts of chlorosulfonic acid are added dropwise to a solution of 250 parts of 1,2-dichloroethane, 93.1 parts of α-picoline and 17.7 parts of isopropylamine in the course of 30 minutes at from −10° to 0° C. The mixture is stirred for 30 minutes, a temperature of about 10° C. being established, after which 15.1 parts of methyl anthranilate are added dropwise in the course of 15 minutes, and stirring is then continued for a further 30 minutes at from 50° to 55° C. 23 parts of phosphorus oxychloride are then added at room temperature, and the reaction mixture is stirred for a further 30 minutes at from 85° to 90° C. and then cooled to about 50° C., 300 parts of water are added and the mixture is then stirred thoroughly for 15 minutes. The phases are separated, and the organic phase is then dried with sodium sulfate and evaporated down in a rotary evaporator.

The residue is treated with 1,000 parts of water, and the product is filtered off and dried. 25.4 parts (88.7% of theory) of 95% pure N-(2-methoxycarbonylphenyl)-N'-isopropylsulfonyldiamide of melting point 102° C. are obtained.

EXAMPLE 7

14 parts of chlorosulfonic acid are added dropwise to a solution of 220 parts of chlorobenzene, 40.6 parts of N,N-dimethyl-N-cyclohexylamine and 7.1 parts of isopropylamine in the course of 30 minutes at from −10° to 0° C. The mixture is stirred for 30 minutes, a temperature of about 10° C. being established, after which 15.1 parts of methyl anthranilate are added dropwise in the course of 15 minutes and stirring is then continued for 30 minutes at from 50° to 55° C. 15.3 parts of phosphorus oxychloride are added at room temperature, and the reaction mixture is stirred for a further 30 minutes at from 85° to 90° C. and then cooled to about 50° C., after which 300 parts of water are added and the mixture is stirred thoroughly for a further 15 minutes. The phases are separated and the organic phase is dried with sodium sulfate and evaporated down.

The residue is treated with 1,000 parts of water, and the product is filtered off and dried. 23.8 parts (84% of theory) of 96% pure N-(2-methoxycarbonylphenyl)-N'-isopropylsulfonyldiamide of melting point 105° C. are obtained.

EXAMPLE 8

17.5 parts of chlorosulfonic acid are added dropwise to a solution of 220 parts of chlorobenzene, 93.1 parts of α-picoline and 19.3 parts of isopropylamine in the course of 30 minutes at from −10° to 0° C. The mixture is stirred for 30 minutes, a temperature of about 10° C. being established, after which 15.1 parts of methyl anthranilate are added dropwise in the course of 15 minutes and stirring is then continued for 30 minutes at from 50° to 55° C. 23 parts of phosphorus oxychloride are added at room temperature, and stirring is continued for a further 30 minutes at from 85° to 90° C. The mixture is cooled to about 50° C., after which 300 parts of water are added and the mixture is stirred thoroughly for a further 15 minutes. The phases are separated and the organic phase is dried with sodium sulfate and then evaporated down.

The residue is taken up in 1,500 parts of $H_2O$, and the product is filtered off and dried. 25.8 parts (90% of theory) of 95% pure N-(2-methoxycarbonylphenyl)-N'-isopropylsulfonyldiamide of melting point 107° C. are obtained.

EXAMPLE 9

23.3 parts of chlorosulfonic acid are added dropwise to a solution of 110 parts of chlorobenzene, 63.5 parts of N,N-dimethyl-N-cyclohexylamine and 19.3 parts of isopropylamine in the course of 30 minutes at from −10° to 0° C. The mixture is stirred for 30 minutes, the temperature increasing to about 10° C., after which 15.1 parts of methyl anthranilate are added dropwise in the course of 15 minutes and stirring is then continued at from 50° to 55° C. 30.6 parts of phosphorus oxychloride are added at room temperature, and stirring is continued for a further 30 minutes at from 85° to 90° C. The mixture is cooled to about 50° C., after which 300 parts of water are added and stirring is continued for a further 15 minutes. The phases are separated and the organic phase is dried with sodium sulfate and evaporated down.

Thorough stirring in 1,000 parts of water at 50° C., and drying, give 27.5 parts (98.9% of theory) of 97.9% pure N-(2-methoxycarbonylphenyl)-N'-isopropylsulfonyldiamide of melting point 107° C.

EXAMPLE 10

23.3 parts of chlorosulfonic acid are added dropwise to a solution of 220 parts of chlorobenzene, 63.5 parts of N,N-dimethyl-N-cyclohexylamine and 19.3 parts of isopropylamine in the course of 30 minutes at 10° C. The mixture is stirred for 30 minutes, the temperature increasing to about 20° C., after which 15.1 parts of methyl anthranilate are added dropwise in the course of 15 minutes and stirring is continued for a further 30 minutes at room temperature. 30.6 parts of phosphorus oxychloride are then added, and stirring is continued for 30 minutes at from 85° to 90° C. The mixture is cooled to about 50° C., after which 300 parts of water are added and stirring is continued for a further 15 minutes. The phases are separated and the organic phase is dried with sodium sulfate and evaporated down.

Thorough stirring of the residue in 1,000 parts of water, and drying, give 27 parts (94.3% of theory) of 95.1% pure N-(2-methoxycarbonylphenyl)-N'-isopropylsulfonyldiamide of melting point 107° C.

EXAMPLE 11

110 parts of chlorobenzene, 63.5 parts of N,N-dimethyl-N-cyclohexylamine and 19.3 parts of isopropylamine are initially taken, and 23.3 parts of chlorosulfonic acid are added dropwise to this solution in the course of 30 minutes at 10° C. The mixture is stirred for 30 minutes, the temperature increasing to about 20° C., after which 15.1 parts of methyl anthranilate are added dropwise in the course of 15 minutes and stirring is then continued for 30 minutes at room temperature.

30.6 parts of phosphorus oxychloride are then added, and stirring is continued for 30 minutes at from 85° to 90° C. The mixture is cooled to about 50° C., after which 300 parts of water are added and stirring is continued for 15 minutes. The phases are then separated and the organic phase is dried with sodium sulfate and evaporated down. The residue is stirred thoroughly in 1,000 parts of water for 1 hour at 50° C., and the product is filtered off under suction and dried. 23.7 parts (96.2% of theory) of 95.6% pure N-(2-methoxycarbonylphenyl)-N'-isopropylsulfonyldiamide of melting point 106° C. are obtained.

EXAMPLE 12

41.4 parts of a dimethylcyclohexylamine/SO₃ adduct are added to a solution of 220 parts of chlorobenzene, 38.1 parts of N,N-dimethyl-N-cyclohexylamine and 19.3 parts of isopropylamine at 0° C., and stirring is continued for 30 minutes at 10° C. 15.1 parts of methyl anthranilate are added dropwise in the course of 15 minutes, the reaction mixture is stirred for a further 30 minutes at from 50° to 55° C. and then cooled, after which 30.6 parts of phosphorus oxychloride are added and stirring is continued for a further 30 minutes at from 85° to 90° C. 300 parts of water are then added at about 50° C., and stirring is continued for 15 minutes.

The phases are separated, and the organic phase is dried with sodium sulfate and evaporated down in a rotary evaporator. The residue obtained is stirred thoroughly for 1 hour at 50° C. in 1,000 parts of water, and the product is filtered off under suction and dried. 26.3 parts (87.9% of theory) of 90.9% pure N-(2-methoxycarbonylphenyl)-N'-isopropylsulfonyldiamide of melting point 103° C. are obtained.

EXAMPLE 13

36.2 parts of a triethylamine/SO₃ adduct are added to a solution of 220 parts of chlorobenzene, 30.3 parts of triethylamine and 19.3 parts of isopropylamine at 0° C., and stirring is continued for 30 minutes at 10° C. 15.1 parts of methyl anthranilate are then added dropwise in the course of 15 minutes, and stirring is continued for 30 minutes at from 50° to 55° C. The mixture is cooled, after which 30.6 parts of phosphorus oxychloride are added and stirring is continued for a further 30 minutes at from 85° to 90° C. 300 parts of water are then added at about 50° C. and the mixture is stirred thoroughly for 15 minutes. The phases are separated, and the organic phase is dried with sodium sulfate and evaporated down. The residue obtained is stirred thoroughly in 1,000 parts of water at 50° C. for one hour, and the product is filtered off under suction and dried. 27.3 parts (95% of theory) of 94.7% pure N-(2-methoxycarbonylphenyl)-N'-isopropylsulfonyldiamide of melting point 108° C. are obtained.

EXAMPLE 14

23.3 parts of chlorosulfonic acid are added dropwise to a solution of 173 parts of ethylene glycol dimethyl ether, 63.5 parts of N,N-dimethylcyclohexylamine and 19.3 parts of isopropylamine in the course of 30 minutes at from −10° to 0° C. Stirring is continued for 30 minutes, the temperature increasing to about 10° C., after which 15.1 parts of methyl anthranilate are added dropwise in the course of 15 minutes and stirring is continued for a further 30 minutes at from 50° to 55° C. The mixture is then cooled to room temperature, 30.6 parts of phosphorus oxychloride are added and stirring is continued for 30 minutes at from 85° to 90° C. The ethylene glycol dimethyl ether is distilled off under reduced pressure, and the residue is stirred thoroughly in 800 parts of water at room temperature. The mixture is filtered under suction, the filtration residue is stirred thoroughly in 1,000 parts of water for a further hour at 50° C., and the product is filtered off under suction and dried. 26.4 parts (94.9% of theory) of 97.8% pure N-(2-methoxycarbonylphenyl)-N'-isopropylsulfonyldiamide of melting point 108° C. are obtained.

EXAMPLE 15

41.4 parts of an N,N-dimethyl-N-cyclohexylamine/SO₃ adduct are added to a solution of 173 parts of ethylene glycol dimethyl ether, 38.1 parts of N,N-dimethyl-N-cyclohexylamine and 19.3 parts of isopropylamine at 0° C., and the reaction mixture is stirred for a further 30 minutes at 10° C. 15.1 parts of methyl anthranilate are then added dropwise in the course of 15 minutes, and stirring is continued at from 50° to 55° C. The mixture is then cooled to room temperature, 30.6 parts of phosphorus oxychloride are added, and stirring is continued for 30 minutes at from 85° to 90° C. The ethylene glycol dimethyl ether is distilled off under reduced pressure, and the residue is stirred thoroughly in 800 parts of water at room temperature. The mixture is filtered under suction, the filtration residue is stirred thoroughly in 1,000 parts of water for a further hour at 50° C., and the product is filtered off under suction and dried. 25.1 parts (89.3% of theory) of 96.8% pure N-(2-methoxycarbonylphenyl)-N'-isopropylsulfonyldiamide of melting point 107° C. are obtained.

EXAMPLE 16

41.4 parts of dimethylcyclohexylamine/SO$_3$ adduct are added to a solution of 132 parts of n-hexane, 38.1 parts of N,N-dimethyl-N-cyclohexylamine and 19.3 parts of isopropylamine at 0° C., the mixture is stirred for 30 minutes at 10° C. and 15.1 parts of methyl anthranilate are then added dropwise in the course of 15 minutes at 10° C. Thereafter, stirring is continued for 30 minutes at from 50° to 55° C., the mixture is cooled to room temperature and 30.6 parts of phosphorus oxychloride are added. Stirring is then continued for 1 hour at 70° C., the n-hexane is distilled off under reduced pressure, the residue is treated with 1,000 parts of water and the product is filtered off and dried. 23.8 parts (78.9% of theory) of 90.2% pure N-(2-methoxycarbonylphenyl)-N'-isopropylsulfonyldiammide of melting point 103° C. are obtained.

EXAMPLE 17

25.6 parts of chlorosulfonic acid are run into a stirred mixture of 55.9 parts of α-picoline and 100 parts of 1,2-dichloroethane in the course of 15 minutes at from −5° to 2° C., and stirring is continued for 15 minutes at 18° C. and 5 minutes at 26° C. Thereafter, 11.8 parts of isopropylamine are added in the course of 15 minutes, the temperature increasing to 42° C. Stirring is continued for 15 minutes, after which 22.7 parts of methyl anthranilate are added in the course of 15 minutes at from 35° to 42° C., and the mixture is stirred for 30 minutes at from 50° to 55° C. 24.6 parts of phosphorus oxychloride are then added in the course of 5 minutes, and the reaction mixture is stirred for 1 hour at from 70° to 75° C., cooled to 30° C. and stirred into 900 parts of ice water, and the aqueous phase separated off is extracted once again with 1,2-dichloroethane. The organic extract is washed twice with 0.5N hydrochloric acid and with water, and is evaporated to dryness. 35 parts (85.7% of theory) of N-(2-methoxycarbonylphenyl)-N'-isopropylsulfonyldiamide of melting point 89°–101° C. are obtained.

EXAMPLE 18

17.6 parts of sulfur trioxide in 80 parts of 1,2-dichloroethane are added to 41 parts of α-picoline at from −5° to +2° C. in the course of 15 minutes. The mixture is stirred for 15 minutes at 6° C., after which 11.8 parts of isopropylamine are added in the course of 15 minutes, the temperature increasing to 35° C. Stirring is continued for 15 minutes, after which 30.2 parts of methyl anthranilate are added in the course of 15 minutes at 35° C., and the mixture is stirred for 30 minutes at from 50° to 55° C. 21.5 parts of phosphorus oxychloride are then run in at from 30° to 40° C. in the course of 5 minutes, and stirring is continued for a further hour at from 70° to 75° C. The reaction mixture is cooled to 40° C. and stirred into 1,000 parts of ice water. The phase separated off is extracted twice more with 1,2-dichloroethane, and the organic extract is extracted three times with 0.5N hydrochloric acid, dried, chromatographed and evaporated down. 41 parts (75.3% of theory) of N-(2-methoxycarbonylphenyl)-N'-isopropylsulfonyldiamide of melting point 96°–102° C. are obtained.

53 parts of a 30% strength by weight sodium methylate solution are added at from 20° to 30° C. to 40 parts of this product, dissolved in 150 parts of methanol. The reaction mixture is stirred under reflux for one hour and then evaporated down under reduced pressure. The residue is taken up in water, the solution is introduced into 200 parts of 2N hydrochloric acid, and the product is filtered off under suction, washed with water and dried. 31.5 parts (89.2% of theory) of 3-isopropyl-1H-2,1,3-benzothiadiazin-4(3H)-one 2,2-dioxide of melting point 127°–132° C. are obtained.

EXAMPLE 19

15.1 parts of methyl anthranilate in 141 g of α-picoline are initially taken, 21 g (0.15 mole) of isopropylsulfamic acid are added at 0° C., and the mixture is stirred for 30 minutes. 10.4 g of isopropylamine are then added dropwise at 30° C., stirring is continued for 30 minutes, 53.7 g of phosphorus oxychloride are added and the mixture is then kept at 80° C. for 2 hours. 1.2 l of water are then added, stirring is continued for 30 minutes and the mixture is left to cool to room temperature. The precipitate which separates out is filtered off under suction, washed with water and dried. 23 g (84.5% of theory) of N-(2-methoxycarbonylphenyl)-N'-isopropylsulfonyldiamide of melting point 106°–107° C. are obtained.

EXAMPLE 20

21 g of isopropylsulfamic acid are added to a solution of 15.1 of methyl anthranilate, 32.6 g of α-picoline and 200 ml of dichloroethane at 0° C., and the mixture is stirred for 30 minutes at room temperature. 24.5 g of phosphorus oxychloride are then added, the mixture is stirred for 90 minutes at 85° C. and then washed twice with water, the organic phase is evaporated down, the residue which remains is suspended in water, and the product is filtered off under suction and dried. 25.2 g (92.6% of theory) of N-(2-methoxycarbonylphenyl)-N'-isopropylsulfonyldiamide of melting point 102°–105° C. are obtained.

EXAMPLE 21

25.45 parts of sulfur trioxide in 130 parts of 1,2-dichloroethane are added to 61.8 parts of α-picoline in 80 parts of 1,2-dichloroethane at −3° C. in the course of 15 minutes, and stirring is continued for 15 minutes, the temperature increasing to 15° C. 17.2 parts of isopropylamine are then added in the course of 15 minutes, the temperature reaching 40° C. The mixture is stirred for 15 minutes at 35° C., after which 31.35 parts of methyl 2-aminonicotinate are added and the mixture is stirred for 30 minutes at from 50° to 55° C. 34 parts of phosphorus oxychloride are then run in at from 25° to 35° C. in the course of 4 minutes, and stirring is continued for one hour at from 70° to 75° C. The reaction mixture is cooled to 30° C. and stirred into 1,000 parts of ice water. The aqueous phase separated off is extracted twice more with 1,2-dichloroethane, and the combined organic extracts are stirred thoroughly twice with 0.5N hydrochloric acid, washed with water, dried over magnesium sulfate and evaporated down. 51.5 parts (91.6% of theory) of N-(3-methoxycarbonylpyrid-2-yl)-N'-isopropylsulfonyldiamide of melting point 98°–108° C. are obtained.

This is dissolved in 280 parts of methanol with the addition of 67.8 parts of 30% strength sodium methylate at from 25° to 30° C., and the mixture is stirred for 1½ hours at 65° C. The reaction mixture is evaporated down under reduced pressure, the residue is taken up in water and the solution is extracted once with diethyl ether and then stirred into 240 parts of 2N hydrochloric acid. The precipitate which separates out is filtered off under suction, washed with water and dried. 35.9 parts (79% of theory) of 3-isopropylpyrido[3,2-e]-2,1,3-thiadiazin-4-one 1,1-dioxide of melting point 192°–200° C. are obtained.

EXAMPLE 22

25.45 parts of sulfur trioxide in 130 parts of 1,2-dichloroethane are added to 61.8 parts of α-picoline in 80 parts of 1,2-dichloroethane at from −5° to 0° C. in the course of 15 minutes, and stirring is continued for 15 minutes, the temperature increasing to 15° C. 17.2 parts of isopropylamine are then added in the course of 15 minutes, the temperature reaching 40° C. The mixture is stirred for 15 minutes at 35° C., after which 34 parts of methyl 3-methyl anthranilate are added, and stirring is continued for 30 minutes at from 50° to 55° C. 34 parts of phosphorus oxychloride are then run in at from 25° to 35° C. in the course of 5 minutes, and stirring is continued for one hour at from 70° to 75° C. The reaction mixture is cooled to 30° C. and stirred into 1,000 parts of ice water. The aqueous phase separated off is extracted twice more with 1,2-dichloroethane, the combined organic extracts are stirred thoroughly twice with 0.5N hydrochloric acid, washed with water, dried over magnesium sulfate and evaporated down. 52.5 parts (89.1% of theory) of N-(2-methoxycarbonyl-6-methylphenyl)-N'-isopropylsulfonyldiamide of melting point 86°–94° C. are obtained.

EXAMPLE 23

17.6 parts of sulfur trioxide in 85 parts of 1,2-dichloroethane are added to a mixture of 51.2 parts of α-picoline and 45 parts of 1,2-dichloroethane at from −2° to 0° C. in the course of 15 minutes, and stirring is continued for 15 minutes, the temperature increasing to 11° C. 27.2 parts of methyl anthranilate are then added in the course of 15 minutes, the temperature reaching 30° C. The mixture is stirred for 15 minutes, after which 23.6 parts of isopropylamine are added in the course of 15 minutes, the temperature increasing to 50° C. Stirring is continued for 30 minutes at from 50° to 55° C., after which the mixture is cooled to 35° C. 30.7 parts of phosphorus oxychloride are then added in the course of 5 minutes, and stirring is continued for one hour at from 70° to 75° C. The reaction mixture is cooled to 30° C. and stirred into 1,000 parts of ice water. The aqueous phase separated off is extracted twice more with 1,2-dichloroethane, and the combined organic extracts are stirred thoroughly twice with 0.5N hydrochloric acid, washed with water, dried over magnesium sulfate and evaporated down. 42.3 parts (86.3% of theory) of N-(2-methoxycarbonylphenyl)-N'-isopropylsulfonyldiamide of melting point 95°–103° C. are obtained.

EXAMPLE 24

23.3 parts of chlorosulfonic acid are added dropwise to a solution of 220 parts of chlorobenzene, 63.5 parts of N,N-dimethyl-N-cyclohexylamine and 19.3 parts of isopropylamine in the course of 30 minutes at from −10° to 0° C. The mixture is stirred for 30 minutes, a temperature of about 10° C. being established, after which 16.5 parts of methyl anthranilate are added dropwise in the course of 15 minutes and stirring is then continued for 30 minutes at from 50° to 55° C. 30.6 parts of phosphorus oxychloride are added at from 20° to 25° C. the mixture is stirred for a further 30 minutes at from 85° to 90° C. and then cooled to about 50° C., 300 parts of water are added, and stirring is continued for a further 15 minutes. The phases are separated, the organic phase is evaporated down, the residue obtained is treated with 1,000 parts of water at 50° C. and the product is filtered off and dried. 28.3 parts (94.9% of theory) of 95.9% pure N-(2-ethoxycarbonylphenyl)-N'-isopropylsulfonyldiamide of melting point 99° C. are obtained.

EXAMPLE 25

23.3 parts of chlorosulfonic acid are added dropwise to a solution of 220 parts of chlorobenzene, 63.5 parts of N,N-dimethyl-N-cyclohexylamine and 19.3 parts of isopropylamine in the course of 30 minutes, during which the temperature is allowed to increase to 55° C. The mixture is stirred for 30 minutes at 55° C., after which 15.1 parts of methyl anthranilate are added dropwise in the course of 15 minutes and the mixture is then stirred for a further 30 minutes at 70° C. 30.6 parts of phosphorus oxychloride are then added dropwise in the course of 10 minutes, the temperature increasing to 110° C. Stirring is continued for 15 minutes at 131° C. and the mixture is cooled to about 50° C., after which 300 parts of water are added and thorough stirring is carried out for 15 minutes. The phases are separated, the organic phase is dried with sodium sulfate and evaporated down, the residue obtained is treated with 1,000 parts of water and the product is filtered off and dried. 20.4 parts (70% of theory) of 93.5% pure N-(2-methoxycarbonylphenyl)-N'-isopropylsulfonyldiamide of melting point 102° C. are obtained.

EXAMPLE 26

23.3 parts of chlorosulfonic acid are added dropwise to a solution of 220 parts of chlorobenzene, 63.5 parts of N,N-dimethyl-N-cyclohexylamine and 19.3 parts of isopropylamine in the course of 30 minutes at from −10° to 0° C. The mixture is stirred for 30 minutes, a temperature of about 10° C. being established, after which 19.3 parts of n-butyl anthranilate are added dropwise in the course of 15 minutes and stirring is then continued for 30 minutes at from 50° to 55° C. 30.6 parts of phosphorus oxychloride are added at from 20° to 25° C., after which stirring is continued for a further 30 minutes at from 85° to 90° C., the mixture is cooled to about 50° C., 300 parts of water are added and thorough stirring is carried out for a further 15 minutes. The phases are separated and the organic phase is dried with sodium sulfate and evaporated down. The crude yield is 35.1 g (95.5% of theory) of 85.4% strength product. Refractive index of a sample obtained by preparative thin layer chromatography (colorless oil) is $n_D^{25} = 1.5189$. The residue obtained (a brown oil) is treated with 1,000 parts of water, and the product is filtered off and dried. 29.5 parts (86.3% of theory) of 91.9% pure N-(2-n-butoxycarbonylphenyl)-N'-isopropylsulfonyldiamide of $n_D^{25} = 1.5200$ are obtained.

EXAMPLE 27

17.5 parts of chlorosulfonic acid are added dropwise to 140 parts of dry α-picoline in the course of 30 minutes, the temperature being maintained at from −5° to +5° C. during this procedure. Stirring is continued for 15 minutes, during which the temperature may increase to 20° C. 15.1 parts of methyl anthranilate are then added in the course of 10 minutes, during which the temperature may increase to 30° C. 19.3 parts of monoisopropylamine are then added in the course of half an hour, during which the reaction mixture is kept at from 30° to 40° C. Stirring is continued for one hour at from 50° to 60° C., the mixture is cooled to room temperature, 23 g (0.15 mole) of phosphorus oxychloride are added, and the mixture is stirred for half an hour at from 85° to 90° C. The reaction mixture is cooled and then diluted with 1 l of ice water, and the residue is filtered off under suction, washed with cold water and dried. 25.3 parts (93% of theory) of 97.5% pure N-(2-methoxycarbonylphenyl)-N'-isopropylsulfonyldiamide of melting point 103° C. are obtained.

EXAMPLE 28

200 parts of tetramethylurea, 63.5 parts of dimethylcyclohexylamine and 19.3 parts of isopropylamine are initially taken, and 23.3 parts of chlorosulfonic acid are then added dropwise to the solution at from −10° to 0° C. in the course of 30 minutes. The mixture is stirred for a further 30 minutes, a temperature of about 10° C. being established, after which 15.1 parts of methyl anthranilate are added dropwise in the course of 15 minutes and stirring is then continued for half an hour at from 50° to 55° C. The mixture is then cooled to room temperature, 30.6 parts of phosphorus oxychloride are added and stirring is continued for half an hour at from 85° to 90° C. The reaction mixture is cooled to room temperature and stirred into 2,000 parts of ice water, and the product is filtered off under suction, washed with water and dried. 25.7 parts (91% of theory) of 96.3% pure N-(2-methoxycarbonylphenyl)-N'-isopropylsulfonyldiamide of melting point 104° C. are obtained.

EXAMPLE 29

220 parts of chlorobenzene, 93.1 parts of β-picoline and 19.3 parts of isopropylamine are initially taken, and 23.3 parts of chlorosulfonic acid are added dropwise to the solution at from −10° to 0° C. in the course of 30 minutes. The mixture is stirred for a further 30 minutes, a temperature of about 10° C. being established, after which 15.1 parts of methyl anthranilate are added dropwise in the course of 15 minutes and stirring is then continued for half an hour at from 50° to 55° C. The mixture is cooled to room temperature, after which 30.6 parts of phosphorus oxychloride are added, and stirring is continued for half an hour at from 85° to 90° C. The reaction mixture is cooled to about 50° C. and stirred thoroughly with 300 parts of water at this temperature for 15 minutes. The phases are separated, the organic phase is evaporated down in a rotary evaporator, the residue is stirred thoroughly in 1,000 parts of water at 50° C. and the product is filtered off under suction and dried. 32.6 parts (75.3% of theory) of 62.8% strength N-(2-methoxycarbonylphenyl)-N'-isopropylsulfonyldiamide of melting point 86° C. are obtained.

We claim:
1. A process for the manufacture of N-phenyl(-pyridyl)-sulfonyldiamides of the formula

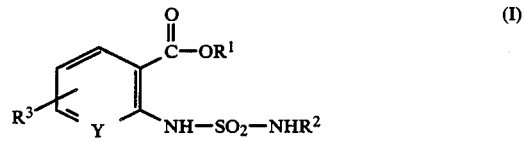

where $R^1$ is hydrogen or $C_1$–$C_5$-alkyl, $R^2$ is $C_1$–$C_5$-alkyl or $C_3$–$C_8$-cycloalkyl, $R^3$ is hydrogen, $C_1$–$C_{10}$-alkyl or $C_1$–$C_4$-haloalkyl and Y is CH or N, wherein an acid derivative of the formula

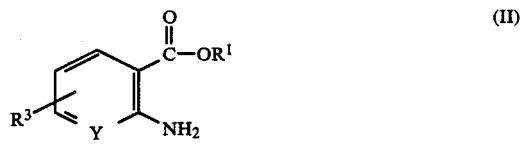

where
$R^1$, $R^3$ and Y have the above meaning, is reacted with a sulfamic acid of the formula

where
$R^2$ has the above meanings, or with a salt of this acid, in the presence of a tertiary amine A, a diluent and a phosphorus halide as a dehydrating agent.

2. A process as set forth in claim 1, wherein a sulfamic acid salt of the formula

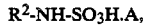

where $R^2$ and A have the meanings given in claim 1, is used.

3. A process as set forth in claim 1, wherein the phosphorus halide is biphosphorus oxychloride.

4. The process of claim 3, wherein the tertiary amine A is a tri-$C_1$–$C_4$-alkyl amine.

5. The process of claim 1, wherein from 1.1 to 3 moles of the sulfamic acid IV is reacted with each mole of acid derivative II.

6. The process of claim 1, wherein the acid derivative II is reacted with a sulfamic acid of the formula

where $R^2$ is $C_1$–$C_5$-alkyl or $C_2$–$C_8$-cycloalkyl, or with a salt of this acid, in the presence of a tertiary amine A, a diluent and a phosphorus halide as a dehydrating agent.

7. The process of claim 1, wherein from 1.1 to 3 moles of the sulfamic acid IV is reacted with each mole of acid derivative II.

* * * * *

UNITED STATES PATENT AND TRADEMARK OFFICE
CERTIFICATE OF CORRECTION

PATENT NO.   : 4,868,308

DATED        : September 19, 1989

INVENTOR(S)  : Hans MERKLE et al.

It is certified that error appears in the above-identified patent and that said Letters Patent is hereby corrected as shown below:

On the title page, "7 Claims" should read --6 Claims--

Claim 3, line 2 should read:

"phorus halide is phosphorus oxychloride"

Please omit Claims 7 as it is identicle to Claim 5.

Signed and Sealed this

Thirteenth Day of November, 1990

Attest:

HARRY F. MANBECK, JR.

*Attesting Officer*      *Commissioner of Patents and Trademarks*